United States Patent
Dutta et al.

(10) Patent No.: US 8,309,910 B2
(45) Date of Patent: Nov. 13, 2012

(54) PHANTOM FOR SPECTRAL CT IMAGE SYSTEM CALIBRATION

(75) Inventors: Sandeep Dutta, Waukesha, WI (US); Naveen Chandra, Kenosha, WI (US); Toshihiro Rifu, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 49 days.

(21) Appl. No.: 12/968,393

(22) Filed: Dec. 15, 2010

(65) Prior Publication Data

US 2012/0155617 A1    Jun. 21, 2012

(51) Int. Cl.
*G12B 13/00* (2006.01)
*G01D 18/00* (2006.01)

(52) U.S. Cl. ............................... 250/252.1; 378/207

(58) Field of Classification Search ............... 250/252.1; 378/207

See application file for complete search history.

(56) References Cited

U.S. PATENT DOCUMENTS

| | | | | |
|---|---|---|---|---|
| 4,724,110 A * | 2/1988 | Arnold | ............... | 264/102 |
| 5,165,050 A * | 11/1992 | Goodenough et al. | ........ | 324/318 |
| 5,907,593 A | 5/1999 | Hsieh et al. | | |
| 5,953,444 A * | 9/1999 | Joseph et al. | ............... | 382/131 |
| 6,298,112 B1 | 10/2001 | Acharya et al. | | |
| 6,775,347 B2 | 8/2004 | Hsieh et al. | | |
| 7,583,777 B2 | 9/2009 | Tang et al. | | |
| 7,774,040 B1 | 8/2010 | Dutta et al. | | |
| 2011/0200244 A1* | 8/2011 | Ashton et al. | ........ | 382/131 |

* cited by examiner

*Primary Examiner* — Kiho Kim
*Assistant Examiner* — Mindy Vu
(74) *Attorney, Agent, or Firm* — Ziolkowski Patent Solutions Group, SC

(57) ABSTRACT

A phantom includes a housing enclosing an interior volume and having a plurality of passages formed therein, wherein each passage is fluidly isolated from the interior volume. First and second inserts are included and configured to be positioned in a first passage of the plurality of passages and include materials having a known material density. The material is selected from iodine, hydroxyapatite (HAP), tricalcium phosphate (TCP), body fat, fatty plaque, sodium chloride (NaCl), gold (Au), and iron (Fe). The material of the inserts can be different materials or the same material at different densities.

22 Claims, 6 Drawing Sheets

# PHANTOM FOR SPECTRAL CT IMAGE SYSTEM CALIBRATION

BACKGROUND OF THE INVENTION

Embodiments of the invention relate generally to CT imaging and, more particularly, to a phantom for spectral CT image system calibration.

Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis that ultimately produces an image.

Generally, the x-ray source and the detector assembly are rotated about the gantry within an imaging plane and around the subject. X-ray sources typically include x-ray tubes, which emit the x-ray beam at a focal point. The detector assembly is typically made of a plurality of detector modules. Data representing the intensity of the received x-ray beam at each of the detector elements is collected across a range of gantry angles. The data are ultimately processed to form an image.

Conventional computed tomography (CT) systems emit an x-ray with a polychromatic spectrum. The x-ray attenuation of each material in the subject depends on the energy of the emitted x-ray. If CT projection data is acquired at multiple x-ray energy levels or spectra, the data contains additional information about the subject or object being imaged that is not contained within a conventional CT image. For example, spectral CT data can be used to produce a new image with x-ray attenuation coefficients equivalent to a chosen monochromatic energy. Such a monochromatic image includes image data where the intensity values of the voxels are assigned as if a CT image were created by collecting projection data from the subject with a monochromatic x-ray beam.

A principle objective of energy sensitive scanning is to obtain diagnostic CT images that enhance information (contrast separation, material specificity, etc.) within the image by utilizing two or more scans at different chromatic energy states. A number of techniques have been proposed to achieve energy sensitive scanning including acquiring two or more scans either (1) back-to-back sequentially in time where the scans require multiple rotations of the gantry around the subject or (2) interleaved as a function of the rotation angle requiring one rotation around the subject, in which the tube operates at, for instance, 80 kVp and 140 kVp potentials.

High frequency generators have made it possible to switch the kVp potential of the high frequency electromagnetic energy projection source on alternating views. As a result, data for two or more energy sensitive scans may be obtained in a temporally interleaved fashion rather than two separate scans made several seconds apart as typically occurs with previous CT technology. The interleaved projection data may furthermore be registered so that the same path lengths are defined at each energy level using, for example, some form of interpolation. Spectral CT data facilitates better discrimination of tissues, making it easier to differentiate between materials such as tissues containing calcium and iodine, for example.

It is important that spectral CT system provide material density images that are accurate. Accordingly, spectral CT systems need to be calibrated to meet the accuracy specifications for different material images. Known calibration methods for the material domain include creating individual material phantoms for a variety of materials and separately analyzing each one. These individual material phantoms are generally created just prior to calibration and are discarded after calibration due since they cannot be stored. The phantom created for one material may vary from the phantom created for the same material at a different time or by a different technician. Additionally, it may be difficult to calibrate a spectral CT system for different patient sizes using such phantoms.

X-ray or CT phantoms for non-spectral CT imaging systems can be made to last a long time. Such phantoms typically comprise synthetic materials configured to mimic the x-ray attenuation of clinically relevant materials such as iodine, fat, water, calcium, and the like in Hounsfield units (HU). However, these synthetic material phantoms fail to accurately mimic the same materials in spectral CT imaging systems. For example, polytetrafluoroethylene (PTFE) or a similar material has been used in the image domain to simulate the HU range of calcium. In the material domain, PTFE fails to mimic calcium.

Therefore, it would be desirable to design a phantom for spectral CT that overcomes the aforementioned drawbacks.

BRIEF DESCRIPTION OF THE INVENTION

In accordance with one aspect, a phantom includes a housing enclosing an interior volume and having a plurality of passages formed therein, wherein each passage is fluidly isolated from the interior volume. A first insert is included and configured to be positioned in a first passage of the plurality of passages and comprising a first material having a known material density of one of iodine, hydroxyapatite (HAP), tricalcium phosphate (TCP), body fat, fatty plaque, sodium chloride (NaCl), gold (Au), and iron (Fe). A second insert is also included and configured to be positioned in a second passage of the plurality of passages and comprising a second material having a known material density of one of iodine, hydroxyapatite (HAP), tricalcium phosphate (TCP), body fat, fatty plaque, sodium chloride (NaCl), gold (Au), and iron (Fe). The known material density of the second material is one of a different material density of a same material as the first material and a known material density of a different material than the first material.

In accordance with another aspect, an apparatus includes a housing having a pair of slots formed therein and having an interior volume hermetically sealed from the pair of slots. A first material insert is configured to be positioned in one of the pair of slots and comprising a known density of a first material selected from the group consisting of iodine, hydroxyapatite (HAP), tricalcium phosphate (TCP), body fat, fatty plaque, sodium chloride (NaCl), gold (Au), and iron (Fe). A second material insert is configured to be positioned in another of the pair of slots and comprising a known density of a second material selected from the group consisting of iodine, hydroxyapatite (HAP), tricalcium phosphate (TCP), body fat, fatty plaque, sodium chloride (NaCl), gold (Au), and iron (Fe). The second material is one of a distinct material from the first material and a same material as the first material.

In accordance with yet another aspect, phantom for spectral CT imaging calibration includes an enclosure enclosing a volume and having a plurality of passages formed therein, wherein the volume is hermetically sealed from the plurality of passages. A first insert is configured to be positioned in a first passage of the plurality of passages and comprising a known density of a first material comprising one of iodine, hydroxyapatite (HAP), tricalcium phosphate (TCP), body fat, fatty plaque, sodium chloride (NaCl), gold (Au), and iron (Fe). A second insert is configured to be positioned in a second passage of the plurality of passages and comprising a known density of a second material different from the first material and comprising one of iodine, hydroxyapatite (HAP), tricalcium phosphate (TCP), body fat, fatty plaque, sodium chloride (NaCl), gold (Au), and iron (Fe). A shell having an opening therein is configured to receive the housing.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

In addition, certain embodiments of the present invention provide systems, methods, and computer instructions for analyzing multi-energy data, such as dual energy data, for example. Certain multi-energy data can be used in spectral imaging systems, such as photon counting systems, for example. Dual energy data, which is a type of multi-energy data, can be embodied in monochromatic images, material density images, and/or effective-Z images. While many of the embodiments described herein are discussed in connection with dual energy data, the embodiments are not limited to dual energy data and can be used in connection with other types of multi-energy data, as one skilled in the art will appreciate. Also, while many of the embodiments discussed herein discussed describe a region of interest that can be selected in an image, a volume of interest can also be selected in an image, as one skilled in the art will appreciate.

Figure 1:
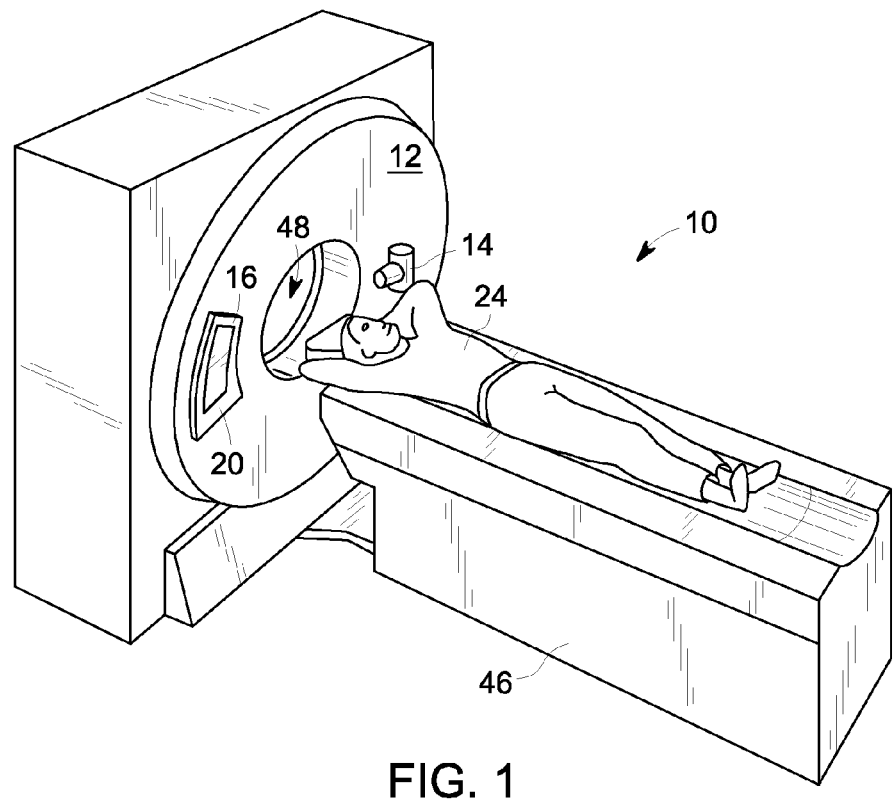
FIG. 1 is a pictorial view of a CT imaging system.
Figure 2:
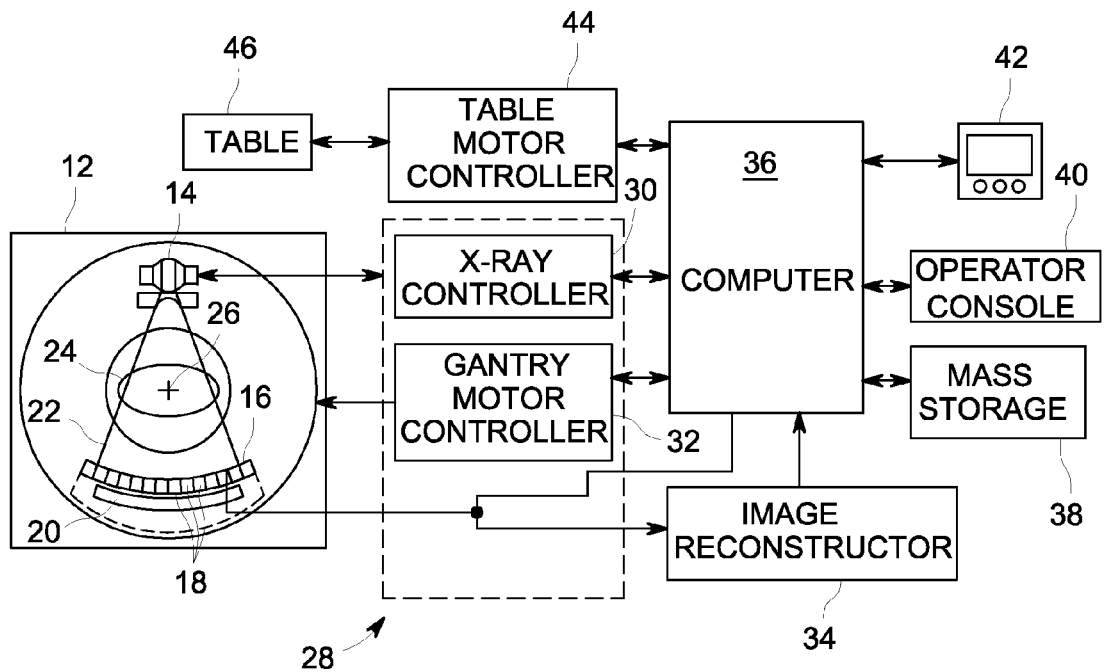
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors 18 and data acquisition systems (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
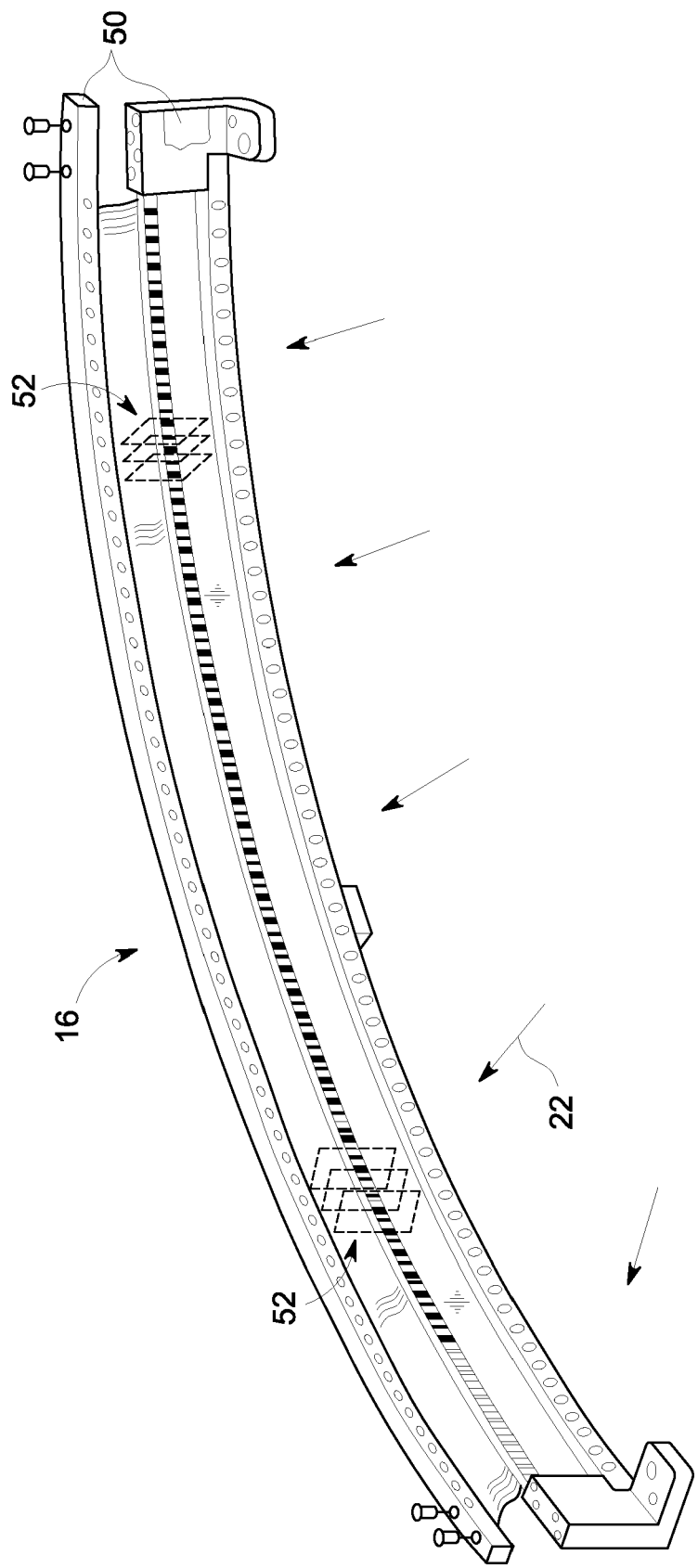
FIG. 3 is a perspective view of one embodiment of a CT system detector array.

As shown in FIG. 3, detector assembly 16 includes rails 50 having collimating blades or plates 52 placed therebetween. Plates 52 are positioned to collimate x-rays 22 before such beams impinge upon, for instance, detector 18 of FIG. 4 positioned on detector assembly 16. In one embodiment, detector assembly 16 includes 57 detectors 18, each detector 18 having an array size of 64×22 of pixel elements 54. As a result, detector assembly 16 has 64 rows and 912 columns (22×57 detectors) which allows 64 simultaneous slices of data to be collected with each rotation of gantry 12.

Figure 4:
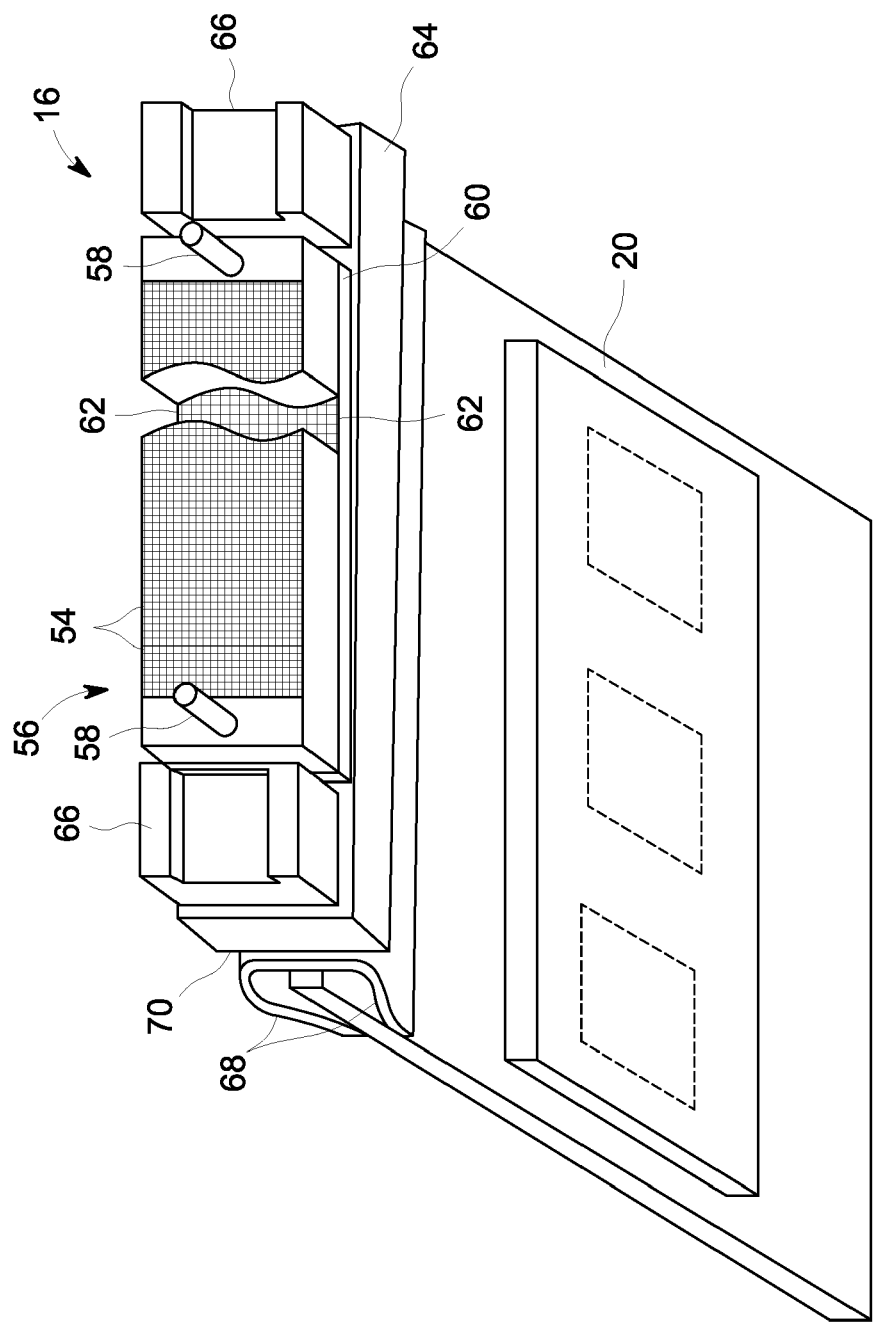
FIG. 4 is a perspective view of one embodiment of a detector.

Referring to FIG. 4, detector 18 includes DAS 20, with each detector 18 including a number of detector elements 54 arranged in pack 56. Detectors 18 include pins 58 positioned within pack 56 relative to detector elements 54. Pack 56 is positioned on a backlit diode array 60 having a plurality of diodes 62. Backlit diode array 60 is in turn positioned on multi-layer substrate 64. Spacers 66 are positioned on multi-layer substrate 64. Detector elements 54 are optically coupled to backlit diode array 60, and backlit diode array 60 is in turn electrically coupled to multi-layer substrate 64. Flex circuits 68 are attached to face 70 of multi-layer substrate 64 and to DAS 20. Detectors 18 are positioned within detector assembly 16 by use of pins 58.

In the operation of one embodiment, x-rays impinging within detector elements 54 generate photons which traverse pack 56, thereby generating an analog signal which is detected on a diode within backlit diode array 60. The analog signal generated is carried through multi-layer substrate 64, through flex circuits 68, to DAS 20 wherein the analog signal is converted to a digital signal.

Figure 5:
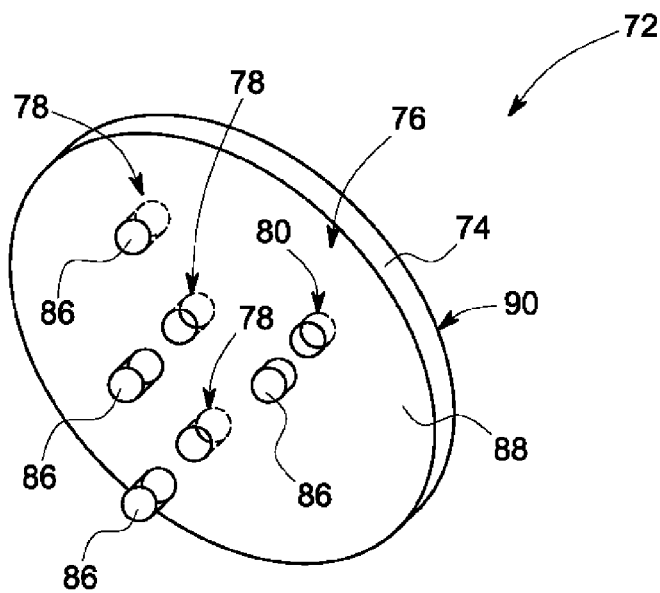
FIG. 5 is a perspective view of a spectral CT phantom in accordance with one embodiment of the present invention.

Referring now to FIG. 5, a phantom 72 for spectral CT image calibration according to an embodiment of the invention is shown. Phantom 72 includes a housing or enclosure 74 having a hollow, interior volume 76. In one embodiment, interior volume 76 is filled with water. A plurality of slots 78-80 formed in housing 74 allow the placement of material inserts 86 therein. Slots 78-80 may extend partially into or all the way through housing 74. As illustrated, slots 78 extend through housing 74 from a first surface or side 88 to a second surface or side 90, and slot 80 extends only partially into housing 74 from first side 88 toward, but not extending through, second side 90. Interior volume 76 is hermetically sealed from the ambient environment and is fluidly isolated from each of the slots 78-80.

Material inserts 86 are solid inserts that contain materials relevant to those materials typically found in imaging patients. For example, material inserts 86 may contain clinically relevant materials such as iodine, hydroxyapatite (HAP) or tricalcium phosphate (TCP), body fat or fatty plaque, sodium chloride (NaCl), or other biomarker materials such as gold (Au) or iron (Fe). These enumerated materials are not exhaustive of the plurality of materials that may be used, however, and embodiments of the invention are not limited to such.

The clinically relevant materials may be suspended and preserved in a matrix to form the solid insert 86. The matrix may be, in an example, a polymer or epoxy matrix. In a preferred embodiment, the matrix is a neutral encapsulant that does not interfere or react with the suspended clinically relevant material. The polymer or epoxy matrix helps ensure that the clinically relevant material suspended therein does not lose its properties over time. Furthermore, the concentration (e.g., mg/cc) of the clinically relevant material in the solid insert 86 is known and can be accounted for during calibration.

In one embodiment, the solid material inserts 86 may be similarly sized so as to be interchangeable with one another and placed in any of the corresponding slots 78 to create a variety of different phantom combinations for calibration. Phantom 72 may thus be customized for particular calibration parameters. In another embodiment, the sizes of one or more of the inserts 86 may be different than other inserts 86 so as to create a larger or smaller quantity of respective clinically relevant material for calibration.

Figure 6:
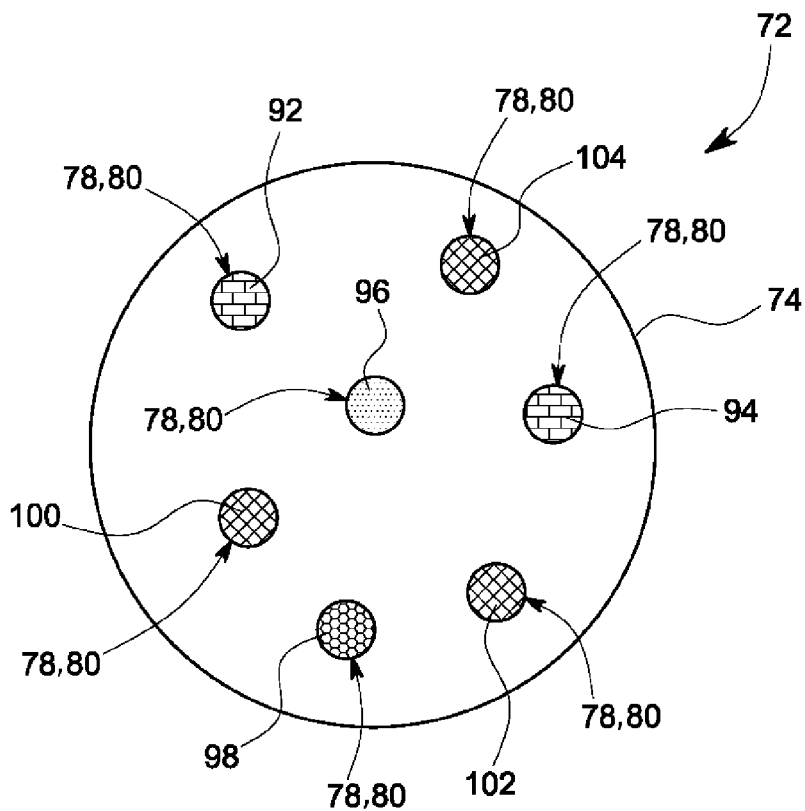
FIG. 6 is a plan view of the spectral CT phantom of FIG. 5 in accordance with one embodiment of the present invention.

As shown in FIG. 6, a plurality of inserts 92-104 of a first combination are positioned in a phantom housing 74 according to one embodiment. Inserts 92-104 are positioned according to a first placement scheme. In this example, inserts 92-94 are calcium inserts having a known density of a calcium material such as HAP or TCP, insert 96 is a soft tissue insert having a known density of water and NaCl, and insert 98 is a fat/oil insert having a known density of fat or oil. Inserts 100-104 include, in this example, iodinated contrast in different known concentrations or densities. Calibration of a spectral CT imaging system using this phantom configuration includes simultaneously calibrating for four different materials and calibrating for three different known concentrations of one of the materials.

Figure 7:
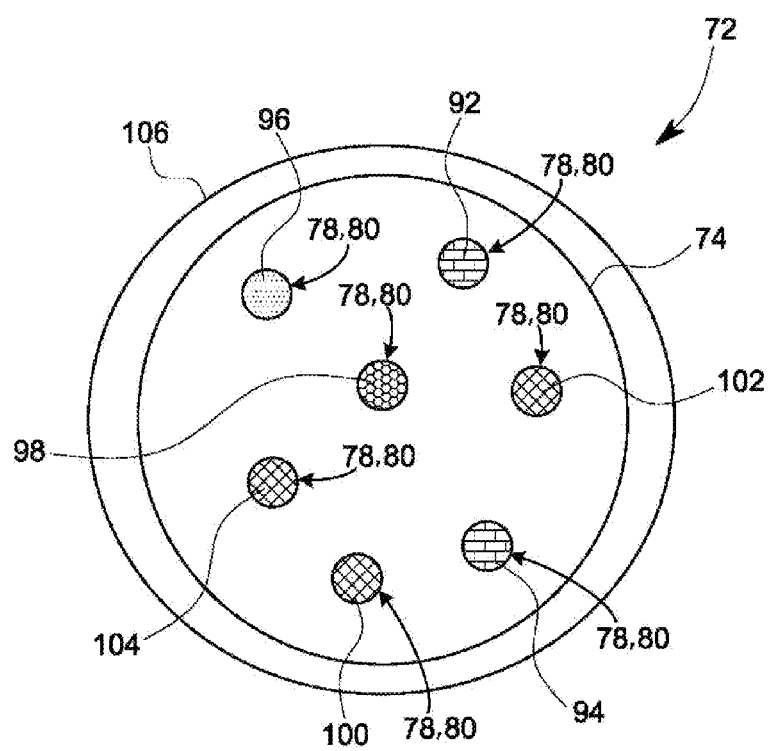
FIG. 7 is a plan view of the spectral CT phantom of FIG. 5 in accordance with another embodiment of the present invention.

FIG. 7 illustrates a placement of the combination of material inserts 92-104 in a second placement scheme according to another embodiment of the invention. As illustrated, inserts 92-104 are re-positioned with respect to that illustrated in FIG. 6. In addition to merely allowing for re-positioning material inserts 92-104 among the various slots 78, 80 a different combination of inserts may be positioned in housing 74. For example, it may be desirable to have only a single type of material insert positioned in housing 74. In this case, one or more inserts of a single material type may be positioned in slots 78, 80. Alternatively, it may be desirable to fill each slot 78, 80 with a combination of material inserts that includes a different material for each of the inserts.

A shell 106 having an opening 108 is also shown in FIG. 7 positioned about housing 74. Shell 106 is removable from housing 74 and attenuates x-rays to simulate a particular patient size. A plurality of shells 106 of various sizes and shapes may be configured to removably engage housing 74 to allow for calibrating the spectral CT imaging system based on a plurality of patient sizes.

Figure 8:
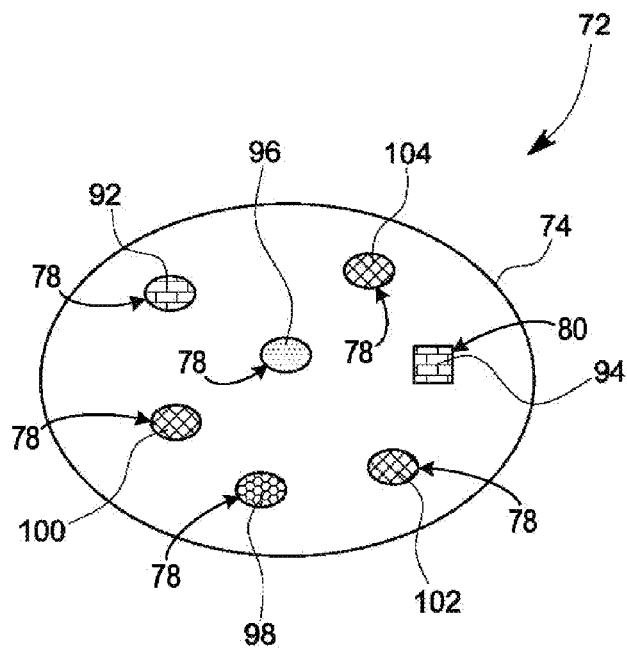
FIG. 8 is a plan view of the spectral CT phantom of FIG. 5 in accordance with another embodiment of the present invention.

Embodiments of the invention include any shape to housing 74 or material inserts 92-104 and passages 78, 80. That is, while the cross-sectional shapes of housing 74 or material inserts 92-104 and passages 78, 80 are illustrated in FIGS. 5-7 as circular cylinders, embodiments of the invention may include other elliptical or polygonal shapes. For example, as shown in FIG. 8, housing 74, material inserts 92-104, and passages 78 are shown as having an elliptical cross-sectional shape, while passage 80 and insert 94 are shown as having a square cross-sectional shape. It is contemplated that any of inserts 92-104 with their respective passages 78, 80 as shown in FIG. 8 may extend either only partially into or completely through housing 74.

Embodiments of the invention allow for switching out the different material concentration modules/inserts for application specific uses including calibration. The phantom described herein allows for assessing the quantitative accuracy and quality of a spectral CT system for different materials at the same time.

While embodiments of the invention are described as being usable with spectral CT image systems, one skilled in the art will recognize that the embodiments of the invention described herein are also applicable to calibration of any imaging system based on x-ray detection. That is, embodiments of the invention described herein may also be used in an x-ray or CT system for calibration based on Hounsfield units.

Figure 9:
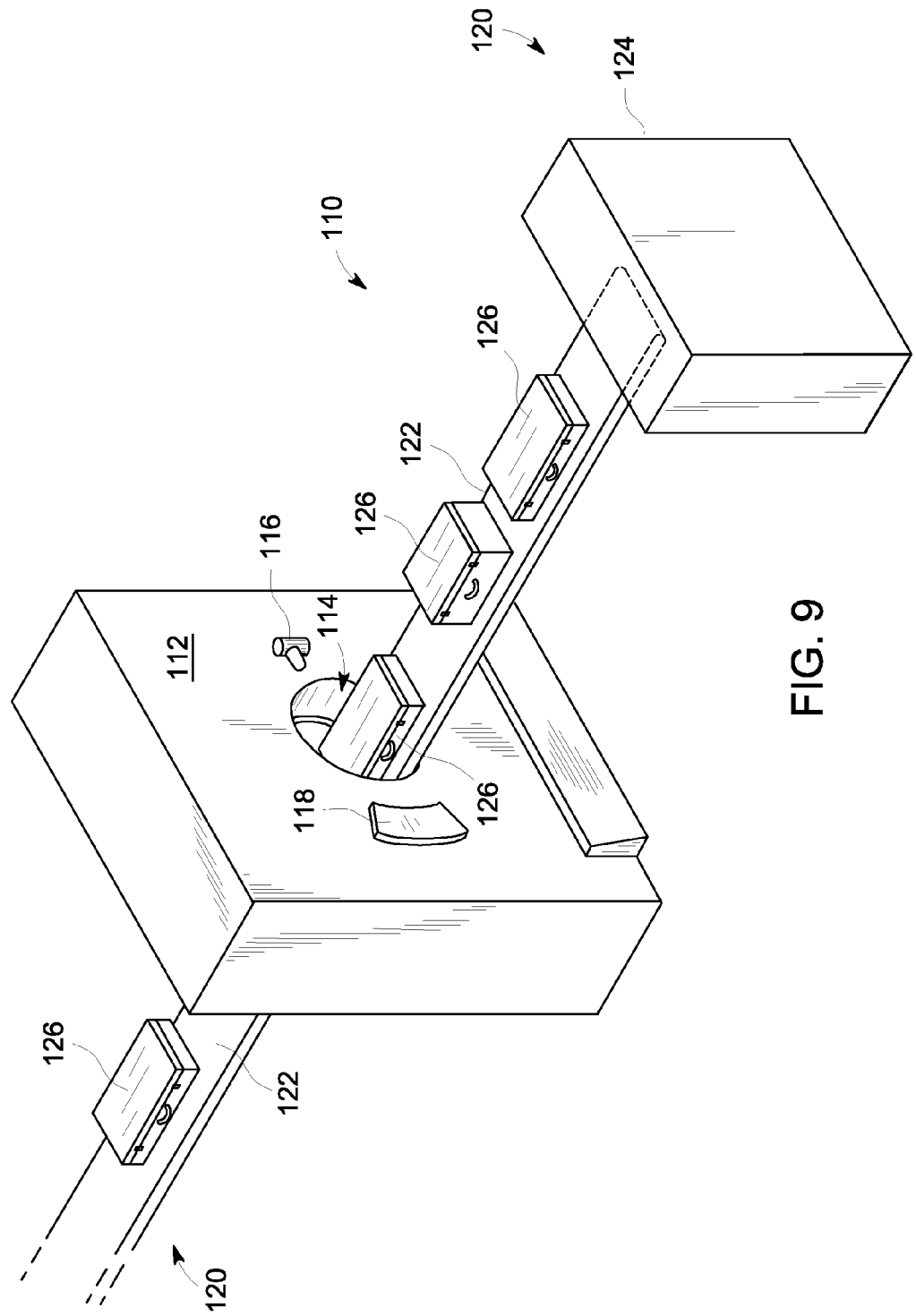
FIG. 9 is a pictorial view of a CT system for use with a non-invasive package inspection system.

Referring now to FIG. 9, package/baggage inspection system 110 includes a rotatable gantry 112 having an opening 114 therein through which packages or pieces of baggage may pass. The rotatable gantry 112 houses a high frequency electromagnetic energy source 116 as well as a detector assembly 118 having scintillator arrays comprised of scintillator cells similar to that shown in FIG. 3 or 4. A conveyor system 120 is also provided and includes a conveyor belt 122 supported by structure 124 to automatically and continuously pass packages or baggage pieces 126 through opening 114 to be scanned. Objects 126 are fed through opening 114 by conveyor belt 122, imaging data is then acquired, and the conveyor belt 122 removes the packages 126 from opening 114 in a controlled and continuous manner. As a result, postal inspectors, baggage handlers, and other security personnel may non-invasively inspect the contents of packages 126 for explosives, knives, guns, contraband, etc.

Therefore, in accordance with one embodiment, a phantom includes a housing enclosing an interior volume and having a plurality of passages formed therein, wherein each passage is fluidly isolated from the interior volume. A first insert is included and configured to be positioned in a first passage of the plurality of passages and comprising a first material having a known material density of one of iodine, hydroxyapatite (HAP), tricalcium phosphate (TCP), body fat, fatty plaque, sodium chloride (NaCl), gold (Au), and iron (Fe). A second insert is also included and configured to be positioned in a second passage of the plurality of passages and comprising a second material having a known material density of one of iodine, hydroxyapatite (HAP), tricalcium phosphate (TCP), body fat, fatty plaque, sodium chloride (NaCl), gold (Au), and iron (Fe). The known material density of the second material is one of a different material density of a same material as the first material and a known material density of a different material than the first material.

In accordance with another embodiment, an apparatus includes a housing having a pair of slots formed therein and having an interior volume hermetically sealed from the pair of slots. A first material insert is configured to be positioned in one of the pair of slots and comprising a known density of a first material selected from the group consisting of iodine, hydroxyapatite (HAP), tricalcium phosphate (TCP), body fat, fatty plaque, sodium chloride (NaCl), gold (Au), and iron (Fe). A second material insert is configured to be positioned in another of the pair of slots and comprising a known density of a second material selected from the group consisting of iodine, hydroxyapatite (HAP), tricalcium phosphate (TCP), body fat, fatty plaque, sodium chloride (NaCl), gold (Au), and iron (Fe). The second material is one of a distinct material from the first material and a same material as the first material.

In accordance with yet another embodiment, phantom for spectral CT imaging calibration includes an enclosure enclosing a volume and having a plurality of passages formed therein, wherein the volume is hermetically sealed from the plurality of passages. A first insert is configured to be positioned in a first passage of the plurality of passages and comprising a known density of a first material comprising one of iodine, hydroxyapatite (HAP), tricalcium phosphate (TCP), body fat, fatty plaque, sodium chloride (NaCl), gold (Au), and iron (Fe). A second insert is configured to be positioned in a second passage of the plurality of passages and comprising a known density of a second material different from the first material and comprising one of iodine, hydroxyapatite (HAP), tricalcium phosphate (TCP), body fat, fatty plaque, sodium chloride (NaCl), gold (Au), and iron (Fe). A shell having an opening therein is configured to receive the housing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A phantom comprising:
a housing enclosing an interior volume and having a plurality of passages formed therein, wherein each passage is fluidly isolated from the interior volume;
a first insert configured to be positioned in a first passage of the plurality of passages and comprising a known density of a first material selected from the group consisting of iodine, hydroxyapatite (HAP), tricalcium phosphate (TCP), body fat, fatty plaque, sodium chloride (NaCl), gold (Au), and iron (Fe);
a second insert configured to be positioned in a second passage of the plurality of passages and comprising a known density of a second material selected from the group consisting of iodine, hydroxyapatite (HAP), tricalcium phosphate (TCP), body fat, fatty plaque, sodium chloride (NaCl), gold (Au), and iron (Fe); and
wherein the known material density of the second material is one of a different material density of a same material as the first material and a known material density of a different material than the first material.

2. The phantom of claim 1 wherein the first and second inserts are solid insert.

3. The phantom of claim 2 wherein the first and second inserts comprise an epoxy.

4. The phantom of claim 3 wherein the first and second materials are suspended in the epoxy.

5. The phantom of claim 1 wherein the first passage extends through the housing from a first side of the housing to a second side of the housing.

6. The phantom of claim 1 wherein a cross-sectional shape of the first insert is configured to match a cross-sectional shape of the first passage.

7. The phantom of claim 6 wherein the cross-sectional shape of the first insert is distinct from a cross-sectional shape of the housing.

8. The phantom of claim 1 further comprising a third insert configured to be positioned in a third passage of the plurality of passages and comprising a first concentration of the first material; and
wherein the first insert comprises a second concentration of the first material, wherein the first and second concentrations are different.

9. The phantom of claim 1 wherein the first insert is further configured to be positioned in the second passage; and
wherein the second insert is further configured to be positioned in the first passage.

10. The phantom of claim 1 further comprising a shell having an opening configured to receive the housing.

11. The phantom of claim 10 wherein the shell is configured to attenuate x-rays.

12. An apparatus comprising:
a housing having a pair of slots formed therein and having an interior volume hermetically sealed from the pair of slots;
a first material insert configured to be positioned in one of the pair of slots and comprising a known density of a first material selected from the group consisting of iodine, hydroxyapatite (HAP), tricalcium phosphate (TCP), body fat, fatty plaque, sodium chloride (NaCl), gold (Au), and iron (Fe);
a second material insert configured to be positioned in another of the pair of slots and comprising a known density of a second material selected from the group consisting of iodine, hydroxyapatite (HAP), tricalcium phosphate (TCP), body fat, fatty plaque, sodium chloride (NaCl), gold (Au), and iron (Fe); and
wherein the second material is one of a distinct material from the first material and a same material as the first material having a distinct known density from the known density of the first material.

13. The apparatus of claim 12 wherein the pair of slots are cylindrically-shaped.

14. The apparatus of claim 12 wherein the pair of slots extend from a first surface of the housing to a second surface of the housing opposite the first surface.

15. The apparatus of claim 12 wherein the first material insert is further configured to be positioned in both slots of the pair of slots.

16. The apparatus of claim 15 further comprising a third material insert configured to be positioned in the one of the pair of slots and comprising a first concentration of the first material; and wherein the first material insert comprises a second concentration of the first material.

17. A phantom for spectral CT imaging calibration comprising:

an enclosure enclosing a volume and having a plurality of passages formed therein, wherein the volume is hermetically sealed from the plurality of passages;

a first insert configured to be positioned in a first passage of the plurality of passages and comprising a known density of a first material comprising one of iodine, hydroxyapatite (HAP), tricalcium phosphate (TCP), body fat, fatty plaque, sodium chloride (NaCl), gold (Au), and iron (Fe);

a second insert configured to be positioned in a second passage of the plurality of passages and comprising a known density of a second material different from the first material and comprising one of iodine, hydroxyapatite (HAP), tricalcium phosphate (TCP), body fat, fatty plaque, sodium chloride (NaCl), gold (Au), and iron (Fe); and a shell having an opening therein and configured to receive the housing.

18. The phantom of claim 17 wherein the enclosure comprises water positioned in the volume.

19. The phantom of claim 17 wherein the enclosure comprises:

a first surface; and a second surface opposite the first surface; and wherein a first passage of the plurality of passages extends from the first surface toward the second surface without reaching the second surface.

20. The phantom of claim 17 wherein the first insert is further configured to be positioned in the second passage, and wherein the second insert is further configured to be positioned in the first passage.

21. The phantom of claim 17 wherein the first material is different from the second material.

22. The phantom of claim 17 wherein the first material is the same as the second material, and wherein the density of the first material is distinct from the density of the second material.

* * * * *